US006645436B2

(12) United States Patent
Davis

(10) Patent No.: US 6,645,436 B2
(45) Date of Patent: Nov. 11, 2003

(54) ESSENTIAL OIL DIFFUSOR

(76) Inventor: Eric A. Davis, 391 N. Mink Creek Rd., Pocatello, ID (US) 83204

( * ) Notice: Subject to any disclaimer, the term of this patent is extended or adjusted under 35 U.S.C. 154(b) by 440 days.

(21) Appl. No.: 09/731,644

(22) Filed: Dec. 6, 2000

(65) Prior Publication Data

US 2002/0068023 A1 Jun. 6, 2002

Related U.S. Application Data

(60) Provisional application No. 60/170,072, filed on Dec. 9, 1999.

(51) Int. Cl.[7] .................................................. A62B 7/08
(52) U.S. Cl. ........................ 422/124; 239/34; 239/8; 239/338; 422/123
(58) Field of Search .............................. 422/4, 5, 122, 422/123, 124, 125; 222/630, 635, 645, 646, 647; 239/6, 8, 34, 270, 338

(56) References Cited

U.S. PATENT DOCUMENTS

| | | | | |
|---|---|---|---|---|
| 4,344,574 A | * | 8/1982 | Meddings et al. | 239/338 |
| D365,628 S | * | 12/1995 | Braun | D23/366 |
| 5,549,247 A | * | 8/1996 | Rossman et al. | 239/57 |
| 5,827,483 A | * | 10/1998 | Fullam | 422/122 |

* cited by examiner

Primary Examiner—Terrence R. Till
Assistant Examiner—Sean E. Conley
(74) Attorney, Agent, or Firm—Hopkins Roden Crockett Hansen & Hoopes, PLLC

(57) ABSTRACT

A diffuser assembly includes a base, oil reservoir, diffusor jet unit, baffled glass top and an electric air pump. The assembly provides a fine aromatic oil mist from the glass top when the jet unit is energized. The baffled glass top locks into a diffusor housing from the top and the oil reservoir threads into the bottom of the housing.

12 Claims, 3 Drawing Sheets

ESSENTIAL OIL DIFFUSOR

PRIORITY CLAIM

This application claims priority of Provisional Application No. 60/170,072 filed Dec. 9, 1999.

TECHNICAL FIELD

This invention relates in general to an essential oil diffusor that atomizes aromatic essential oils.

SUMMARY OF THE INVENTION

An essential oil diffusor (a.k.a. diffuser) to dispense natural essential oils into the atmosphere. It is the most effective way to finely vaporize essential oils without harming or altering their vital components and valuable properties. It does not heat the oil during the process. This diffusor is a very effective tool for diffusing essential oils with their fragrances and therapeutic properties.

This essential oil diffusor consists of the following components: a highly efficient compact diffusor jet; an oil reservoir (i.e., essential oil bottle); an oil reservoir base; and glass top. A separate electric air pump and air line tubing provides air from the air pump to the diffusor jet.

Other objects, advantages and capabilities of the present invention will become more apparent as the description proceeds.

DETAILED DESCRIPTION OF THE INVENTION

Figures 1, 2:
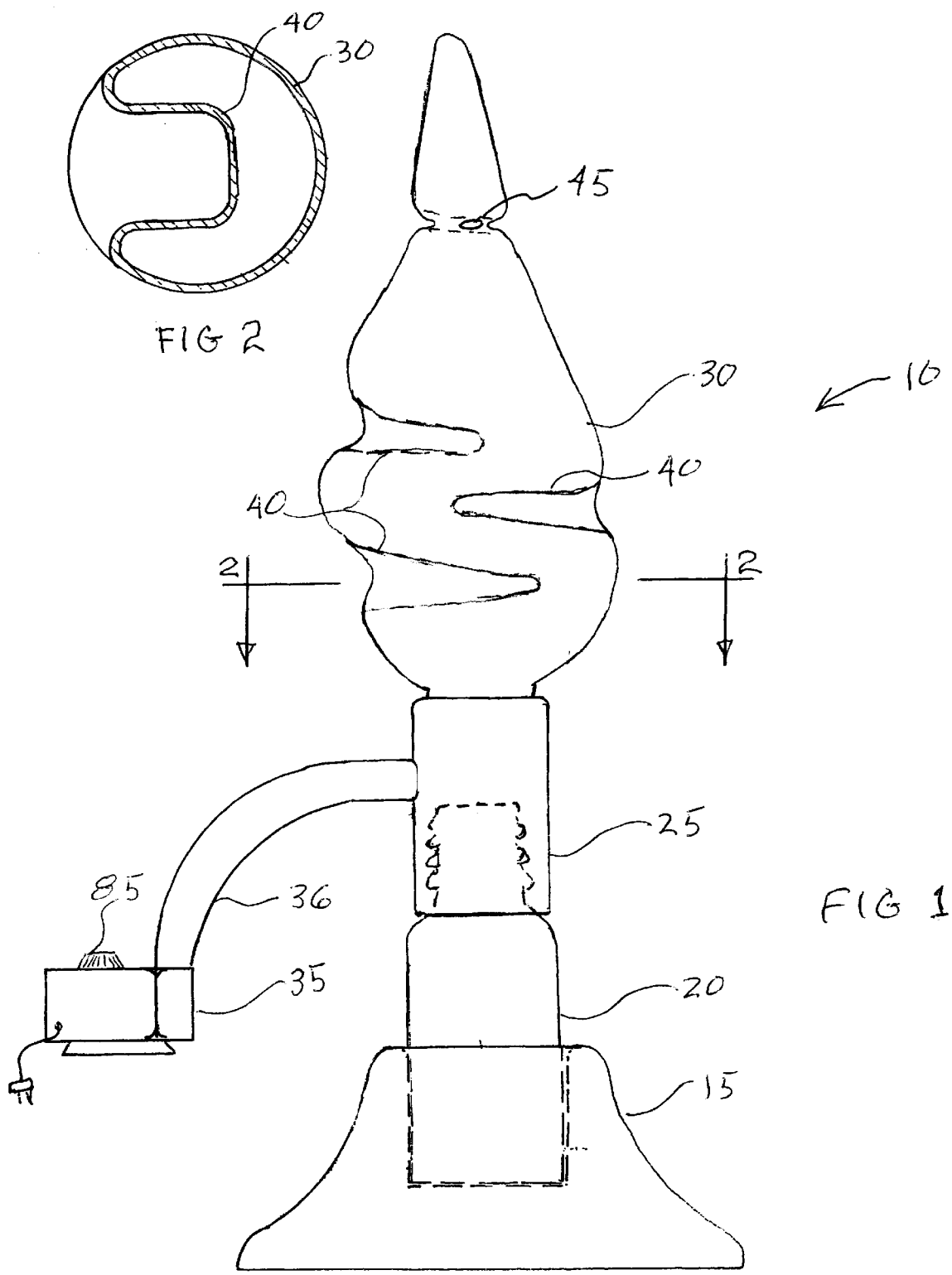
FIG. 1 is a front elevation of the diffusor assembly.
FIG. 2 is a top section view taken along lines 2—2 of FIG. 1.

FIG. 1 illustrates the oil diffusor assembly 10, which includes the base 15, oil reservoir 20, diffusor housing 25, glass top 30 and air pump 35. The electric air pump 35 supplies air at about 3±0.5 psi via tube 36 to diffusor housing 25. The air aspirates the oil from the oil reservoir 20 through jets within the diffusor housing 25 and into the glass top 30. The glass top 30 has three baffles 40 or tongues, protruding part way into the interior of the glass top 30 as shown in section in FIG. 2. The air and aspirated oil exits the glass top 30 at the pair of apertures 45 (one shown) near the top of the glass.

Figure 3:
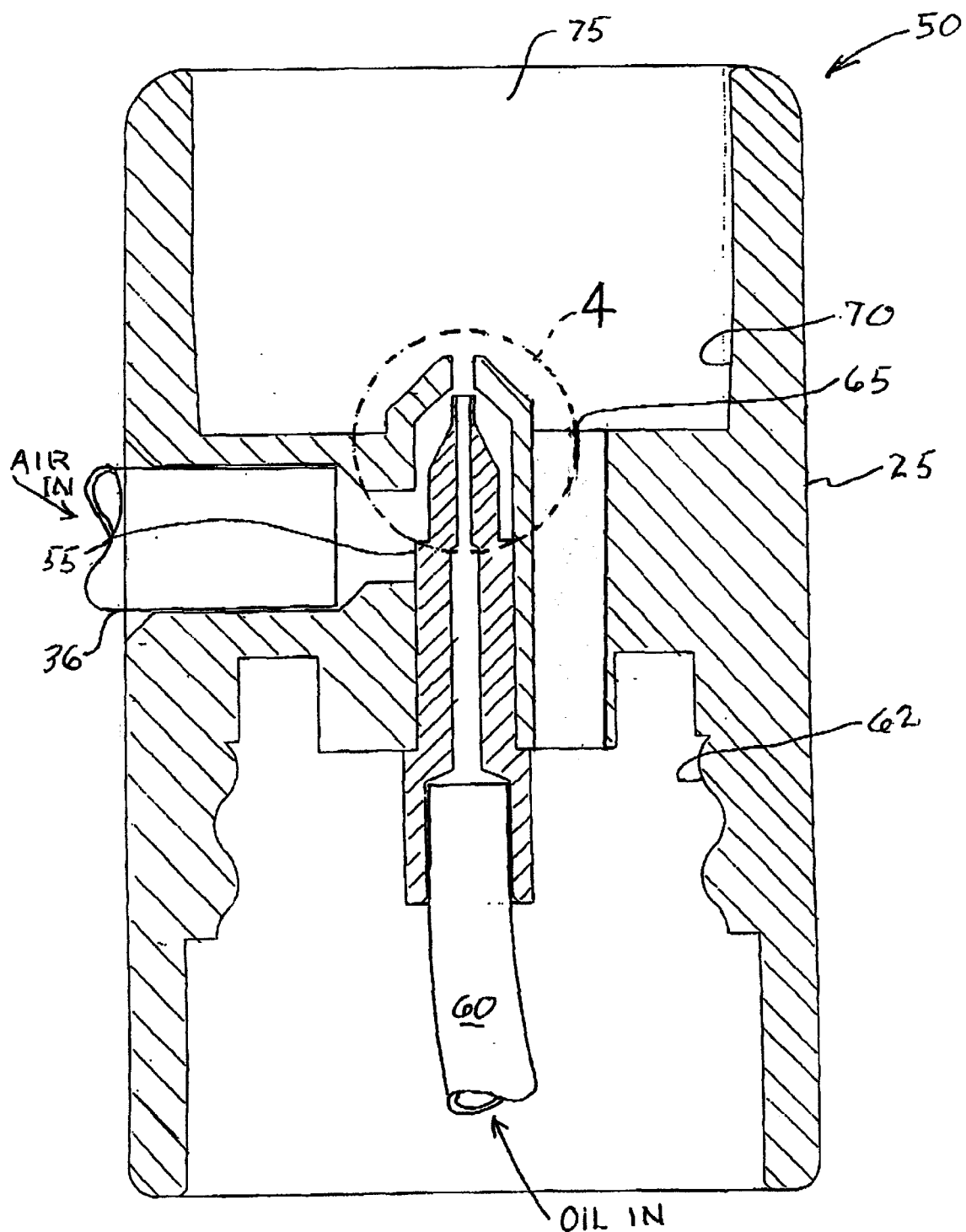
FIG. 3 is a front section of the diffusor jet unit.

The details of the diffusor jet unit 50 can be seen in side-section view FIG. 3. This unit consists of the diffusor housing 25, a diffusor oil jet 55 and a reservoir tube 60 which transports the oil from the reservoir 20 to the oil jet 55. The lower inner wall of the housing 25 has threads 62 that engage similar threads on the glass jar reservoir. The housing 25 has three oil drain holes 65 (one shown) at an upper base section of the diffusor housing 25. The upper inner wall of the housing 25 is tapered at 20 to firmly engage the glass top 30 (FIG. 1) when it is inserted within the upper housing opening 75.

The enlarged section view (without hatching) illustrates the critical dimension of the jet 55 that creates the fine oil mist during operation. Jet tip I.D. "A" is about 0.59 mm and jet tip O.D. "B" is about 0.8 mm. The housing tip I.D. "C" is about 0.81 mm and the housing tip thickness "D" is about 1.14 mm. The jet tip height "E" is about 0.99 mm and the distance "F" from the top of jet tip to top of housing tip 80 is about 1.52 mm.

Figure 5:
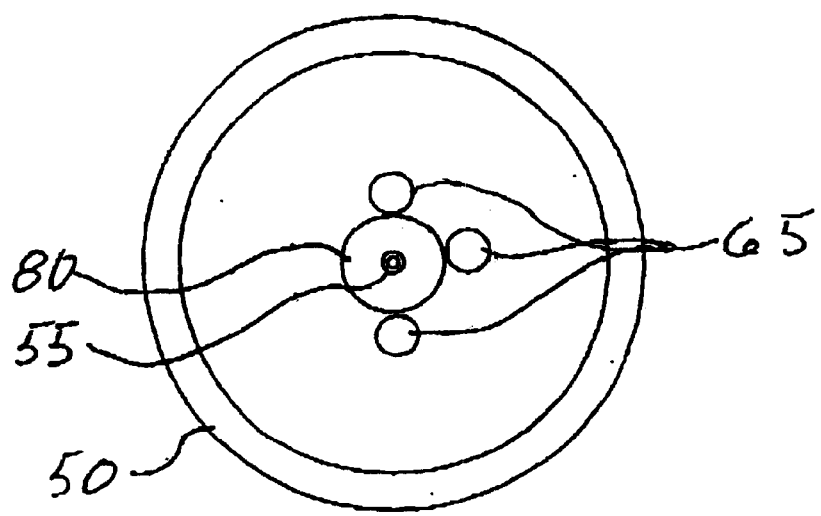
FIG. 5 is a top view of the diffusor jet unit.
Figure 4:
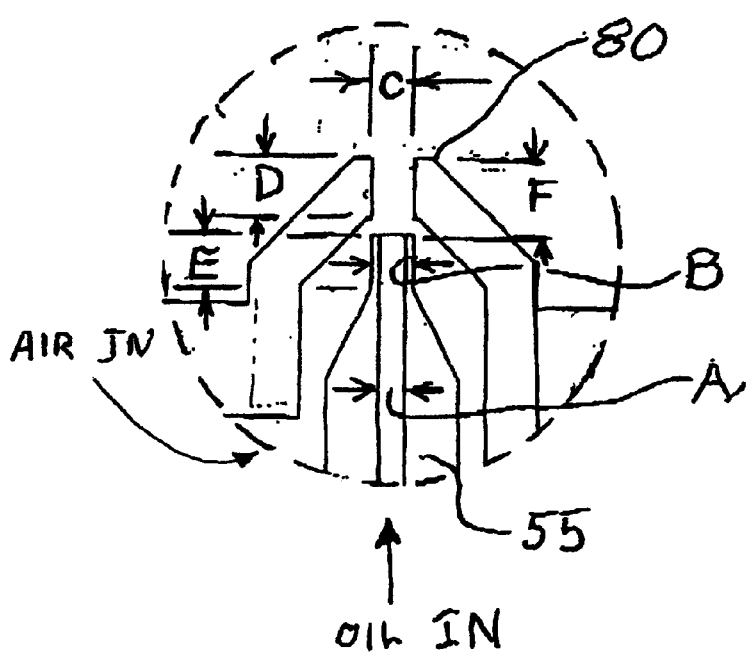
FIG. 4 is an enlarged front section view of the diffusor jet unit.

The FIG. 5 top view of the jet unit shows the jet 55 within the diffusor 50. The housing tip 80 is above and surrounds the jet 55. This view shows all three oil drain holes 65.

The diffusor assembly 10 operates by mixing air with essential oil to produce an extremely fine mist of vapor which disperses in the air via apertures 45. The air is supplied to the diffusor jet 55 from an air pump 35 attached by air line tubing 36. The oil is supplied from the oil reservoir 20 through an oil tube 60. As the air passes through the diffusor jet 55 it causes a vacuum in the oil tubing and oil reservoir 20 causing the essential oil to be drawn up through the oil tubing into the diffusor jet 55. The oil is then diffused into the air and pushed into the glass top 30. The unique design of the glass top, i.e., the baffles 40, then separates and returns to the oil reservoir 20, any essential oil vapor that may not be fine enough. The fine mist is then dispersed into the atmosphere through the openings 45 in the top of the glass 30. The amount of fine mist dispersed can be adjusted by adjusting the air flow via the air pump adjusting knob 85 (FIG. 1).

The diffusor housing 25 is compact and made to tightly thread directly on the essential oil bottle reservoir 20. The housing 25 is made out of an inert plastic.

The essential oil diffusor wooden base is designed to hold the diffusor housing 25 in place and reduce the possibility of the diffusor assembly 10 being tipped or knocked over. It also adds to the overall look and beauty of the diffusor.

An optional deluxe box base is a wooden box with opening lid which contains the complete diffusor assembly (air pump, oil reservoir, tubing etc.). It has a lid on top that slides off to reveal diffusor assembly inside. It has a cloth lining and a foam cutout pad to hold the diffusor oil reservoir and four bottles of essential oil blends as well as the pump. The power cord for the air pump comes out of a small hole in the end of the box near the bottom so it can be plugged in and so the on/off switch is readily available. It has a place on top from which the glass top extends to disperse the essential oil mist. It is designed to be aesthetically pleasing and extremely practical. It provides an extremely sturdy base to hold the diffusor so that it is difficult to knock over. It has also been designed so that it does not transfer the vibrations of the pump but helps to further quiet the diffusor.

The oil reservoir 20 is a glass bottle that is made of tinted glass to protect the essential oils from long term exposure to light rays that can harm essential oils. Both the diffusor housing 25 and the diffusor base 15 have been manufactured to fit the glass bottle reservoir 20 specifically.

The glass top 30 is made of Pyrex™ glass which is formed into the unique drop shape design and then tempered for strength in an 1800° F. scientific kiln. The unique design reduces spills, breakage, and noise. The main function of the glass top 30 is to separate the heavier mist from the ultra fine mist, thus improving the quality of dispersed mist and the efficiency of the diffusor. Since only the ultra fine mist is dispersed, while the rest of the mist is returned to the oil reservoir, this diffusor uses very minimal essential oil to cover a large area. This ultra fine mist is also unique in that it is "lighter than air". In other words, it dissipates into the air instead of settling down onto the furniture, appliances, etc. This feature dramatically reduces possible damage to furniture finishes etc.

The air pump 35 is the source of air for the diffusor assembly 10 and is the only electric part of the diffusor. It is quiet, compact and it is designed to last for years.

The tubing 60 used for the oil supply is specially selected because of its ability to resist caustic oils and its flexibility.

What is claimed is:

1. An essential oil diffusor assembly comprising:
   a) a base;
   b) an oil reservoir fitted in the base;
   c) a diffusor jet unit threaded on the oil reservoir;
   d) an electric air pump flexibly attached to the diffusor jet unit; and
   e) a baffled glass top affixed within a top of the diffusor jet unit said V glass top containing a plurality of baffles extending partly across an interior of said glass top.

2. The diffusor jet unit of claim 1 further comprising:
   a) a diffusor housing having an air inlet aperture on a side of the housing;
   b) an oil jet affixed within the housing directly below a housing tip;
   c) an oil tube affixed to the oil jet; and
   d) multiple oil drain holes adjacent to the housing tip.

3. The diffusor jet unit of claim 2 wherein the jet further comprises: a jet tip having an inside diameter of about 0.59 mm; an outside diameter of about 0.8 mm; and a jet tip height of about 0.99 mm.

4. The diffusor jet unit of claim 3 wherein the housing tip further comprises:
   a) a housing tip inside diameter of about 0.81 mm;
   b) a housing tip thickness of about 1.14 mm; and
   c) a distance from the jet tip to the housing tip of about 1.52 mm.

5. The diffusor assembly of claim 2 wherein the diffusor housing is made of plastic, the reservoir is made of glass and the base is made of wood.

6. An essential oil diffusor assembly comprising:
   a) a wooden base;
   b) a glass oil reservoir fitted in the base;
   c) a diffusor jet unit threaded on the oil reservoir;
   d) an electric air pump flexibly attached to the diffusor jet unit; and
   e) a baffled glass top affixed within a top of the diffusor jet unit, said glass top having three baffles extending partially across an interior of the glass top.

7. The diffusor jet unit of claim 6 further comprising:
   a) a diffusor housing having an air inlet aperture on a side of the housing;
   b) an oil jet affixed within the housing directly below a housing tip;
   c) an oil tube affixed to the oil jet; and
   d) multiple oil drain holes adjacent to the housing tip.

8. The diffusor assembly of claim 6 wherein the glass top has a pair of apertures at a top of the glass top.

9. The diffusor jet unit of claim 7 wherein the oil jet further comprises: a jet tip having an inside diameter of about 0.59 mm; an outside diameter of about 0.8 mm; and a jet tip height of about 0.99 mm.

10. The diffusor jet unit of claim 9 wherein the housing tip further comprises:
    a) a housing tip inside diameter of about 0.81 mm;
    b) a housing tip thickness of about 1.14 mm; and
    c) a distance from the jet tip to the housing tip of about 1.52 mm.

11. An essential oil diffusor assembly comprising:
    a) abase;
    b) an oil reservoir fitted in the base;
    c) a diffusor jet unit threaded on the oil reservoir;
    d) an electric air pump flexibly attached to the diffusor jet unit; and
    e) a baffled glass top affixed within a top of the diffusor jet unit, wherein the baffled glass top has three baffles extending partially across an interior of the glass top.

12. The diffusor assembly of claim 11 wherein the glass top has a pair of apertures at a top of the glass top.

* * * * *